United States Patent
Alferness et al.

(10) Patent No.: US 7,270,676 B2
(45) Date of Patent: Sep. 18, 2007

(54) MITRAL VALVE THERAPY DEVICE, SYSTEM AND METHOD

(75) Inventors: Clifton A. Alferness, Redmond, WA (US); John M. Adams, Sammamish, WA (US); John Melmoth Power, Melbourne (AU)

(73) Assignee: Cardiac Dimensions, Inc., Kirkland, WA (US)

( * ) Notice: Subject to any disclaimer, the term of this patent is extended or adjusted under 35 U.S.C. 154(b) by 426 days.

(21) Appl. No.: 10/925,570

(22) Filed: Aug. 24, 2004

(65) Prior Publication Data

US 2005/0038507 A1   Feb. 17, 2005

Related U.S. Application Data

(62) Division of application No. 09/855,945, filed on May 14, 2001, now Pat. No. 6,800,090.

(51) Int. Cl.
*A61F 2/24* (2006.01)

(52) U.S. Cl. .................. 623/2.36; 623/904

(58) Field of Classification Search ...... 623/2.36–2.37, 623/2.11; 606/108
See application file for complete search history.

(56) References Cited

U.S. PATENT DOCUMENTS

| | | | |
|---|---|---|---|
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,474,557 A | 12/1995 | Mai | |
| 5,514,161 A | 5/1996 | Limousin | |
| 5,554,177 A | 9/1996 | Kieval et al. | |
| 5,562,698 A | 10/1996 | Parker | |
| 5,584,867 A | 12/1996 | Limousin et al. | |
| 5,601,600 A | 2/1997 | Ton | |
| 5,676,671 A | 10/1997 | Inoue | |

(Continued)

FOREIGN PATENT DOCUMENTS

EP   0893133 A1   1/1999

(Continued)

OTHER PUBLICATIONS

Papageorgiou, P., et al., "Coronary Sinus Pacing Prevents Induction of Atrial Fibrillation," Circulation 96: 1893-1898, Sep. 16, 1977.

*Primary Examiner*—Suzette Gherbi
(74) *Attorney, Agent, or Firm*—Shay Law Group LLP

(57) ABSTRACT

An assembly and method for effecting the condition of a mitral valve annulus of a heart includes a guide wire configured to be fed into the coronary sinus of the heart, and a mitral valve annulus therapy device configured to be slidingly received on the guide wire and advanced into the coronary sinus of the heart on the guide wire. A guide tube may further be employed for guiding the device into the coronary sinus. An introducer which may be employed for pushing the device into or pulling device out of the heart has a mechanism for releasably locking to the device. This enables substitution of the device if needed. Also, the crossover point of the circumflex artery and coronary sinus may be determined and avoided when the device is deployed.

11 Claims, 5 Drawing Sheets

U.S. PATENT DOCUMENTS

| | | |
|---|---|---|
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,961,545 A | 10/1999 | Lentz et al. |
| 5,984,944 A | 11/1999 | Forber |
| 6,027,517 A | 2/2000 | Crocker et al. |
| 6,077,295 A | 6/2000 | Limon et al. |
| 6,077,297 A | 6/2000 | Robinson et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,190,406 B1 | 2/2001 | Duerig et al. |
| 6,210,432 B1 | 4/2001 | Solem et al. |
| 6,275,730 B1 | 8/2001 | KenKnight et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,656,221 B2 | 12/2003 | Taylor et al. |
| 6,676,702 B2 * | 1/2004 | Mathis ............ 623/2.36 |
| 6,716,158 B2 | 4/2004 | Raman et al. |
| 6,718,985 B2 | 4/2004 | Hlavka et al. |
| 6,723,038 B1 | 4/2004 | Schroeder et al. |
| 6,764,510 B2 | 7/2004 | Vidlund et al. |
| 6,790,231 B2 | 9/2004 | Liddicoat et al. |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0004572 A1 | 1/2003 | Goble et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0088305 A1 | 5/2003 | Van Schie et al. |
| 2003/0105520 A1 | 6/2003 | Alferness et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0171776 A1 | 9/2003 | Adams et al. |
| 2003/0171806 A1 | 9/2003 | Mathis et al. |
| 2003/0212453 A1 | 11/2003 | Mathis et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0111095 A1 | 6/2004 | Gordon et al. |
| 2004/0127980 A1 | 7/2004 | Kowalsky et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis et al. |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis |
| 2004/0220657 A1 | 11/2004 | Nieminen et al. |
| 2004/0243227 A1 | 12/2004 | Starksen et al. |
| 2004/0243228 A1 | 12/2004 | Kowalsky et al. |
| 2004/0249452 A1 | 12/2004 | Adams et al. |
| 2004/0260342 A1 | 12/2004 | Vargas et al. |
| 2005/0027351 A1 | 2/2005 | Reuter et al. |

FOREIGN PATENT DOCUMENTS

| | | |
|---|---|---|
| EP | 1050274 A1 | 11/2000 |
| EP | 1095634 A2 | 5/2001 |
| GB | 0741604 | 12/1955 |
| WO | WO98/56435 A1 | 12/1998 |
| WO | WO 00/44313 A1 | 8/2000 |
| WO | WO 00/60995 A3 | 10/2000 |
| WO | WO 01/00111 A1 | 1/2001 |
| WO | WO01/30248 | 5/2001 |
| WO | WO 01/50985 A1 | 7/2001 |
| WO | WO 01/54618 A1 | 8/2001 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/049647 A1 | 6/2003 |
| WO | WO 03/059198 A2 | 7/2003 |
| WO | WO 03/063735 A2 | 8/2003 |
| WO | WO 04/045463 A2 | 6/2004 |
| WO | WO2004/084746 | 10/2004 |

* cited by examiner

MITRAL VALVE THERAPY DEVICE, SYSTEM AND METHOD

CROSS-REFERENCE

This application is a divisional application of Ser. No. 09/855,945, filed May 14, 2001, now U.S. Pat. No. 6,800, 090 which is incorporated herein by reference in its entirety, and to which application we claim priority under 35 USC § 121.

FIELD OF THE INVENTION

The present invention generally relates to a device, system and method for treating a deformed heart valve. The present invention more particularly relates to a device, system and method for constricting or reforming a mitral valve annulus from within the coronary sinus to correct mitral valve dilation without blocking blood flow in the circumflex artery and which may be implemented using a guide wire within the coronary sinus to effect accurate device deployment and substitution.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members maybe formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus or at least a portion of it to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. The device is implanted using an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Unfortunately, the human anatomy does impose some obstacles to this recently proposed procedure for treating mitral regurgitation. More specifically, the human heart includes a coronary artery which descends from the aorta. One branch of the coronary artery is the circumflex artery which, in turn, includes the left marginal branch of the circumflex artery. As used herein, the term "circumflex artery" is taken to include the circumflex artery itself or any branch therefrom. The circumflex artery extends distally generally along the coronary sinus but at a point proximal to the coronary artery, it passes under the coronary sinus. The circumflex artery supports blood flow important to the viability of the heart. Hence, reduction in this blood flow must be avoided. As a result, a device placed in the coronary sinus must not be permitted to extend within the coronary sinus beyond the crossover point of the circumflex artery and the coronary sinus to avoid constriction of the circumflex artery. This contemplates the need to know the location of the circumflex artery and coronary sinus crossover point. It also contemplates accurate positioning of the device within the coronary sinus to assure that the device does not extend over the circumflex artery.

The above is further compounded by the fact that the human heart anatomy and indeed the mitral valve condition will vary from patient to patient. Hence, after deployment of an initial therapy device, the initial device effectiveness must be tested. Should a further device having different properties or configuration be deemed more efficacious, there must be provided a way to easily remove the initial device and then deploy the further device with the same deployment accuracy to avoid the crossover of the circumflex artery with the coronary sinus.

The present invention addresses these issues. The present invention provides a therapy system and procedure which enables avoidance of the crossover of the circumflex artery with the coronary sinus by permitting accurate placement of an initial device or any substitute device within the coronary sinus. Further to that end, the present invention enables the crossover point of the circumflex artery with the coronary sinus to be readily determined and, if desired, continuously observed during the therapy procedure. Still further, the present invention contemplates a mitral valve therapy device which is configured to avoid constricting the circumflex artery even though it passes over the circumflex artery within the coronary sinus.

SUMMARY OF THE INVENTION

The present invention provides an assembly for effecting the condition of a mitral valve annulus of a heart. The assembly includes a guide wire configured to be fed into the coronary sinus of the heart and a mitral valve annulus therapy device configured to be slidably received on the guide wire and advanced into the coronary sinus of the heart on the guide wire.

The assembly may further include an elongated introducer configured to be slidably received on the guide wire proximal to the device. The introducer may be releasably locked to the device during the deployment of the device within the coronary sinus. The assembly may further include a guide tube having an inner lumen dimensioned for receiving the guide wire and the device and introducer when the device and introducer are slidingly received on the guide wire.

The assembly may still further include an elongated flexible member which is visible under X ray fluoroscopy and which may be advanced into the circumflex artery. The guide wire may also be visible under X ray fluoroscopy to reveal, under X ray fluoroscopic examination, the crossover point of the circumflex artery and the coronary sinus.

The present invention still further provides a mitral valve annulus device for reshaping the mitral valve annulus to effect the condition of a mitral valve annulus of a heart. The device includes a resilient member having a cross sectional dimension for being received within the coronary sinus of a heart and having a longitudinal dimension having an arched configuration for partially encircling the mitral valve and exerting an inward pressure on the mitral valve when within the coronary sinus adjacent the mitral valve for reshaping at least a portion of the mitral valve annulus. The device includes a distal end having a bent portion to avoid exerting pressure on the circumflex artery at the crossover point of the circumflex artery and the coronary sinus.

The present invention further provides a mitral valve annulus therapy device including a generally C-shaped clip member formed of resilient material for exerting a substantially radially inward force on the mitral valve annulus when placed in the coronary sinus of a heart about and adjacent to the mitral valve. The device has a distal end including a bent portion to avoid exerting pressure on the circumflex artery at the crossover point of the circumflex artery and the coronary sinus.

The present invention further provides a method of determining the crossover point of the circumflex artery and coronary sinus of a heart. The method includes the steps of inserting a first elongated flexible rod into the coronary sinus, the first rod being visible under X ray fluoroscopy, inserting a second elongated flexible rod into the circumflex artery, the second rod being visible under X ray fluoroscopy, and subjecting the heart to X ray fluoroscopic examination to determine the crossover point of the first and second rods.

The present invention further provides a method of deploying a mitral valve annulus reshaping device within the coronary sinus of a heart. The method includes the steps of inserting a guide wire into the coronary sinus of the heart, and advancing an elongated mitral valve annulus constricting device on the guide wire and into the coronary sinus into a position such that the device at least partially encircles the mitral valve of the heart.

The advancing step may further include the steps of slidingly mounting an elongated flexible introducer onto the guide wire proximal to the device, engaging the distal end of the introducer with the proximal end of the device, and pushing the device distally into the coronary sinus with the introducer. After the device is deployed in the coronary sinus, the introducer may be withdrawn.

During deployment of the device, the introducer may be releasably locked to the device. After deployment, but before the introducer is withdrawn, the introducer may be released from the device.

The method may further include the steps of providing an elongated flexible guide tube having an inner lumen, the inner lumen having a cross sectional dimension greater than the cross sectional dimension of the guide wire, and feeding the guide tube into the coronary sinus of the heart over the guide wire with the guide wire within the inner lumen of the guide tube. Thereafter, the device may be pushed along the guide wire and within the guide tube.

The present invention further provides a method of deploying a mitral valve annulus therapy device within the coronary sinus of a heart. The method includes the steps of inserting a first wire into the circumflex artery of the heart, the first wire being visible under X ray fluoroscopy, inserting a second wire into the coronary sinus of the heart, the second wire being visible under X ray fluoroscopy, subjecting the heart to X ray fluoroscopic examination to visualize the crossover point of the first and second wires, and deploying an elongated mitral valve annulus therapy device within the coronary sinus in a position such that the distal end of the device is proximal to the crossover point of the first and second wires. Preferably, during deployment, the device is guided by the second wire into the coronary sinus.

The method may further include the steps of slidingly mounting an elongated flexible introducer onto the second wire proximal to the device, engaging the distal end of the introducer with the proximal end of the device, and pushing the device distally into the coronary sinus with the introducer. During deployment, the introducer may be releasably locked to the device. After deployment, the introducer may be released from the device and withdrawn.

The method may further include the steps of providing an elongated flexible guide tube having an inner lumen, the inner lumen having a cross sectional dimension greater than the cross sectional dimension of the second wire, and the guide tube being transparent to X ray fluoroscopy, and feeding the guide tube into the coronary sinus of the heart over the second wire with the second wire within the inner lumen of the guide tube. The device may then be pushed along the second wire by the introducer and within the guide tube until it reaches a desired position within the coronary sinus.

The present invention still further provides a method of deploying a constricting device within the coronary sinus of a heart to reshape the mitral valve annulus of the heart. The method includes the steps of providing an elongated flexible guide wire having a cross sectional dimension, feeding the guide wire into the coronary sinus of the heart, providing an elongated flexible guide tube having an inner lumen, the inner lumen having a cross sectional dimension greater than the cross sectional dimension of the guide wire, and feeding the guide tube into the coronary sinus of the heart over the guide wire with the guide wire within the inner lumen of the guide tube.

The method further includes the steps of providing a mitral valve annulus constricting device configured to be slidingly received on the guide wire and within the inner lumen of the guide tube, the device including a proximal end, providing a flexible elongated introducer configured to be slidingly received on the guide wire and within the inner lumen of the guide tube, the introducer having a distal end, and placing the device onto the guide wire.

The method still further includes the steps of placing the introducer onto the guide wire, engaging the distal end of the introducer with the proximal end of the device, pushing the device with the introducer in a distal direction along the guide wire and within the guide tube until the device is at least partially encircling the mitral valve within the coronary sinus of the heart, and withdrawing the introducer and the guide tube from the heart.

During deployment of the device, the introducer may be releasably locked to the device. After deployment, but before the introducer is withdrawn, the introducer may be released from the device. The effectiveness of the device may then be tested.

Should a replacement device be required, further steps to replace the device with a substitute device may be taken. Those steps may include feeding the guide tube into the coronary sinus of the heart over the guide wire and the device, feeding the introducer over the guide wire and into the guide tube, releasably locking the distal end of the introducer to the proximal end of the device, and retracting the introducer and device in a proximal direction and from the guide tube. When the device has been removed, a replacement device may then be deployed in the same manner as the initial device was deployed.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, and the several figures of which like reference numerals identify identical elements, and wherein:

DETAILED DESCRIPTION OF THE INVENTION

Figure 1:
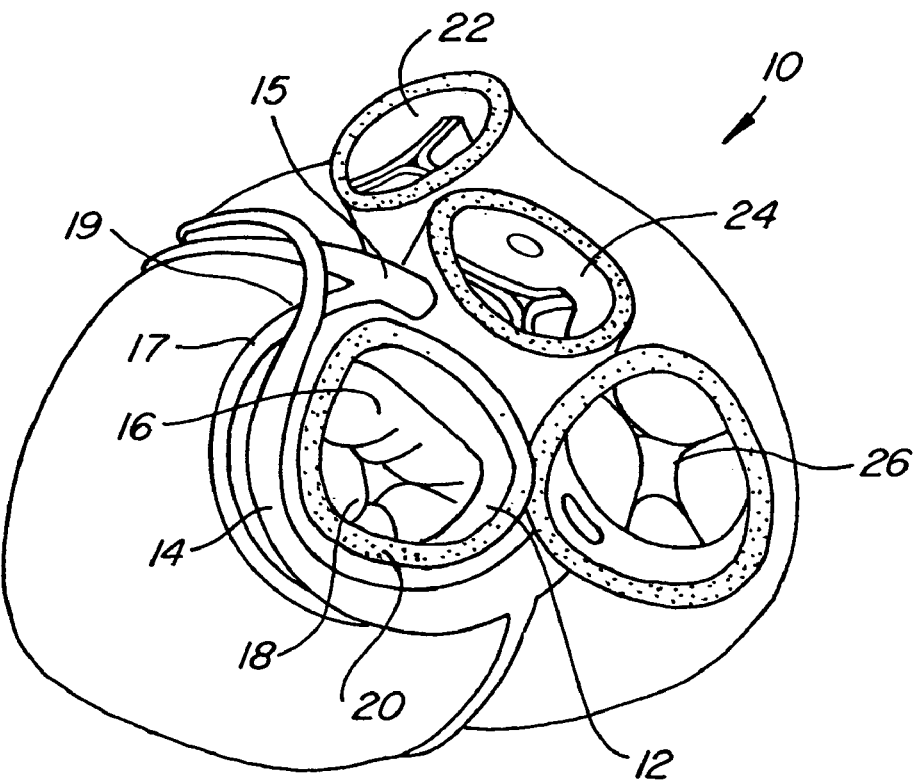
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Of particular importance is the physiological relationship of the coronary sinus 14 and the circumflex artery 17. The circumflex artery 17 branches from the coronary artery 15 and supplies blood flow to critical tissue of the heart 10. The circumflex artery passes beneath the coronary sinus 14 at a crossover point 19. It is one aspect of the present invention to avoid constriction of blood flow through the circumflex artery 17 when a mitral valve therapy device is deployed in the coronary sinus 14.

Figure 2:
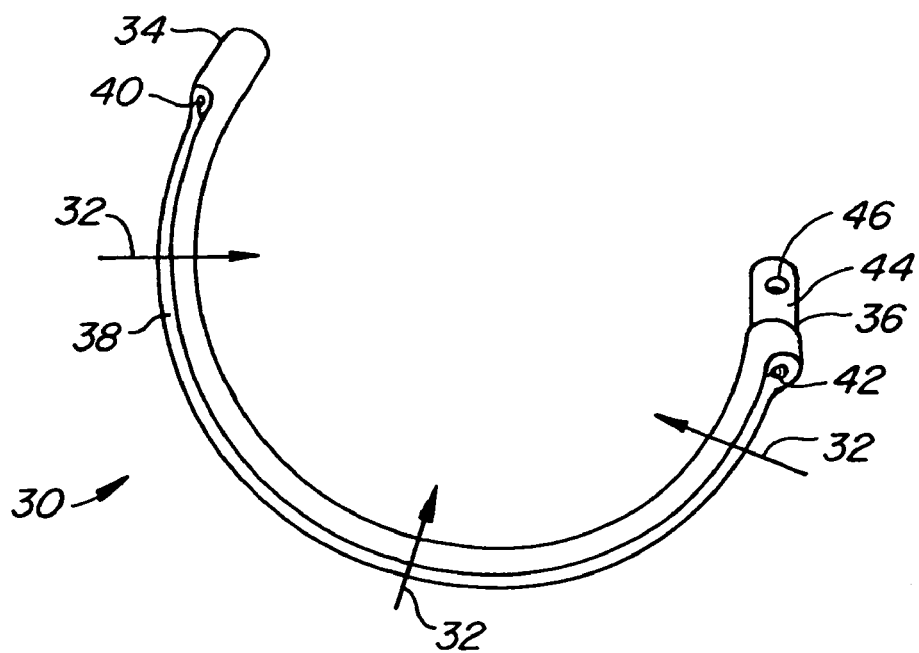
FIG. 2 is a perspective view of a mitral valve annulus constricting device embodying the present invention.

FIG. 2 shows a mitral valve therapy device 30 embodying the present invention. As may be noted in FIG. 2, the device is elongated and has an arched configuration to at least partially encircle the mitral valve 12 adjacent to the mitral valve annulus 20 when implanted in the coronary sinus 14. The device 30 has an unstressed preformed arched radius smaller than the radius of the dilated mitral valve annulus 20. This causes the device 30 to constrict the mitral valve annulus and impart an inward, generally radial force designated by arrows 32 on the mitral valve annulus 20 when implanted in the coronary sinus of the heart. This force reshapes and returns the mitral valve annulus 20 to its original or substantially original geometry to permit the cusps 16 and 18 to more fully come together for sealing the left atrium during left ventricular contraction.

The device 30 has a cross section dimension to be received by the coronary sinus. It is preferably formed of a resilient material permitting the device to be straightened and/or bent for being advanced into the coronary sinus. After being positioned within the coronary sinus, the device is permitted to assume its preformed arched configuration to act upon the mitral valve annulus as previously described. To that end, the device may be formed of, for example, Nitinol, a nickel titanium alloy, well known in the art. This material, as is well known, is capable of being preformed but manipulated to be straight or partially bent while having sufficient memory to return to its preformed configuration. Stainless steel is also among the materials which may be used in forming the device 30. In order to be received within the coronary sinus, the device may have a cross sectional dimension of, for example, on the order of four or five french.

With continued reference to FIG. 2, the device 30 has a distal end 34 and a proximal end 36. Between the distal end 34 and proximal end 36 the device further includes a channel 38 which is aligned with a bore 40 extending through the distal end 34 and a bore 42 extending through the proximal end 36. The proximal end 36 further includes an integral sleeve 44 which carries a protruding locking pin 46. As will be seen subsequently, the bores 40 and 42 permit the device to be slidingly received by a guide wire during deployment of the device 30. The guide wire, during deployment, is confined within the channel 38.

Figure 3:
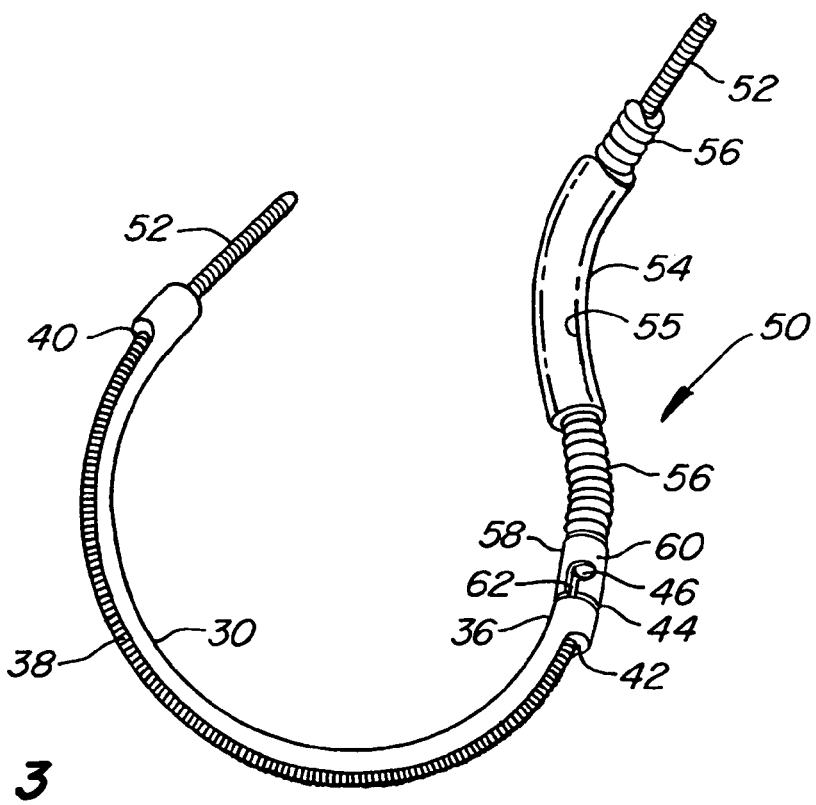
FIG. 3 is a perspective view of an assembly for deploying a mitral valve constricting device in accordance with a preferred embodiment of the present invention.
Figure 4:
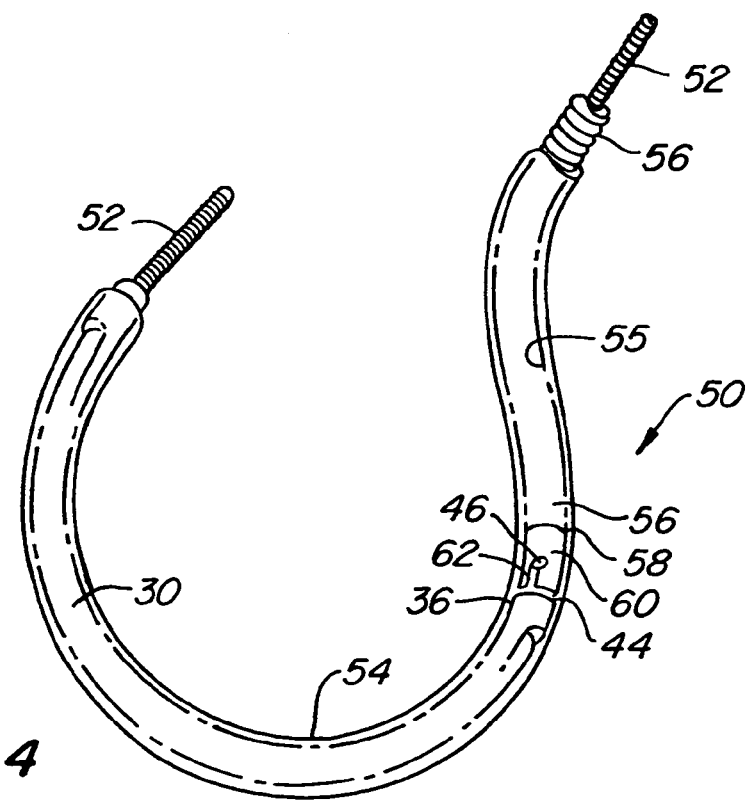
FIG. 4 is another perspective view of the assembly of FIG. 3.

FIGS. 3 and 4 illustrate an assembly 50 for deploying or implanting the mitral valve therapy device 30. The assembly 50 includes a guide wire 52, a guide tube 54, and an elongated introducer 56.

The guide wire 52 is preferably an elongated coil. It has an outer dimension to permit the guide wire 52 to be passed through the bores 40 and 42 of the device 30. This enables the device 30 to be slidingly received on the guide wire 52 with the guide wire confined within the channel 38 of the device 30.

The guide tube 54 is elongated and formed of a flexible biocompatible material. It includes an inner lumen 55 permitting the device 30 and the introducer 56 to be received therein.

The introducer 56 preferably takes the form of an elongated coil having an inner channel dimensioned to be received by and slid onto the guide wire 52. At a distal end 58 the introducer includes a sleeve 60 which may be received over the sleeve 44 of the device 30. The introducer sleeve 60 includes a detented slot 62 for releasably receiving the pin 46 of the device 30. This enables the introducer 56 to be releasably locked to the device 30 during deployment of the device. It also permits the introducer to be relocked to the device 30 for extracting the device should it be necessary to remove the device 30 for exchange with another device.

Figure 5:
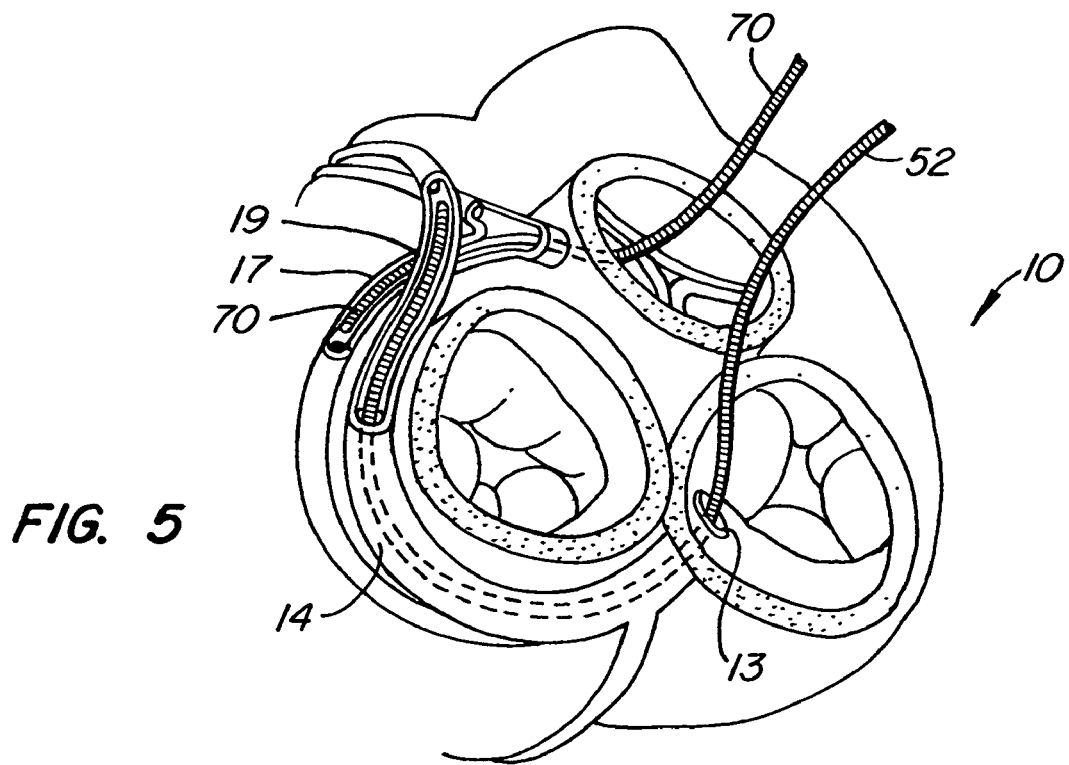
FIG. 5 is a superior view of a human heart similar to that of FIG. 1 and illustrating a method of determining the crossover point of the circumflex artery and the coronary sinus in accordance with a preferred embodiment of the present invention.
Figure 6:
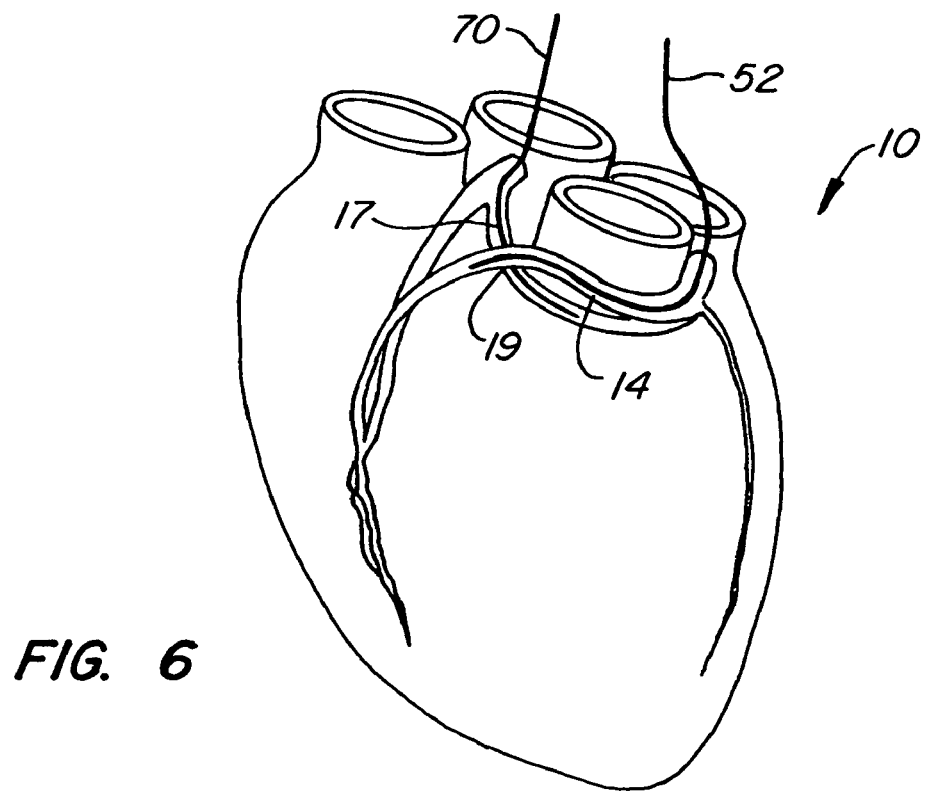
FIG. 6 is another view of a human heart illustrating the method of determining the crossover point of the circumflex artery and the coronary sinus in accordance with the present invention.

As previously mentioned, the circumflex artery 17 passes under the coronary sinus 14. When the device 30 is deployed, it should not be permitted to exert a force from the coronary sinus against the circumflex artery. Hence, in accordance with one embodiment of the present invention, the device is implanted within the coronary sinus at a position whereby the distal end 34 of the device 30 is proximal to the crossover point of the circumflex artery and the coronary sinus. This requires determination of the crossover point. FIGS. 5 and 6 illustrate how such a determination may be made in accordance with the present invention.

A first elongated member, such as an elongated wire or coil wire 70 is inserted into the circumflex artery 17. The wire 70 may be formed of a material visible under X ray fluoroscopy or be of other material having a coating which is visible under X ray fluoroscopy. Next, a second wire which may be the guide wire 52 is inserted into the coronary sinus 14 by way of the ostium of coronary sinus 13. Again, the wire 52 is preferably of a material visible under X ray fluoroscopy or of another material having a coating which is visible under X ray fluoroscopy. Preferably, the wires 52 and 70 are elongated coils formed of stainless steel.

The heart 10 or at least that portion of the heart 10 where the circumflex artery passes under the coronary sinus is subjected to X ray fluoroscopy. X ray fluoroscopy is well known in the art. The crossover point 19 where the wires 52 and 70 cross and hence where the circumflex artery and coronary sinus cross may then be readily observed by X ray fluoroscopic examination. This locates the crossover point 19 which is to be distal to the distal end 34 of the device 30 when the device 30. is positioned within the coronary sinus.

Once the crossover point 19 has been determined, the device 30 may be deployed. During the deployment of the device, the first wire 70 may be left in the circumflex artery to permit continuous X ray fluoroscopic examination or later X ray fluoroscopic examination to confirm proper device positioning.

Figure 7:
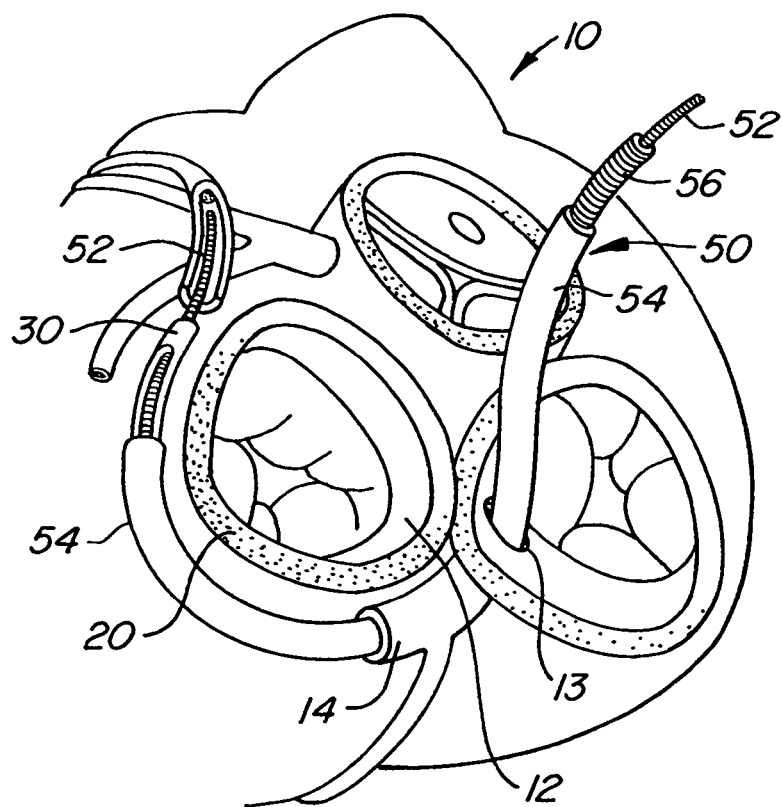
FIG. 7 is another superior view of a human heart illustrating deployment of a mitral valve therapy device in accordance with the preferred embodiment of the present invention.

FIG. 7 shows how the assembly 50 may be used to implant the device 30. Presumably the guide wire 52 has already been positioned in the coronary sinus 14 to support the determination of the circumflex artery and coronary sinus crossover point as described above. As also described above, wire 70 may also be left in the heart at this time.

Next, the guide tube 54 is advanced into the heart. The guide tube is advanced over the guide wire 52. The guide wire hence guides the guide tube 54 into the coronary sinus where the device is to be implanted.

When the guide tube 54 is positioned in the coronary sinus, the device 30 and introducer 56 are then advanced into the guide tube 54 and over the guide wire 52. The distal end 58 of the introducer 56 is first releasably locked to the proximal end 36 of the device 30 (FIGS. 3 and 4) by advancing the sleeve 60 of the introducer 56 over the sleeve 44 of the device 30 and inserting the locking pin 46 in the detented locking groove 62.

With the distal end of the introducer 56 thus engaged with the proximal end of the device 30, the device may then be pushed by the introducer 56 into the coronary sinus 14 while being guided by both the guide wire 52 and the guide tube 54.

When the device is positioned within the coronary sinus 14 with its distal end proximal to the crossover point 19 and its position is confirmed by X ray fluoroscopy, the introducer may be removed. This is accomplished by turning the introducer to unlock the pin 46 and retracting the introducer from the guide tube. Then, the guide tube 54 may also be retracted leaving the device in place but still on the guide wire 52. The performance of the device 30 may now be evaluated. If another device of different properties is deemed more appropriate, the device may be readily replaced. Thus is accomplished by reinserting the guide tube over the device, reinserting the introducer, locking the introducer to the device, and removing the device through the guide tube with the introducer. A new device may then be deployed as previously described.

Figure 8:
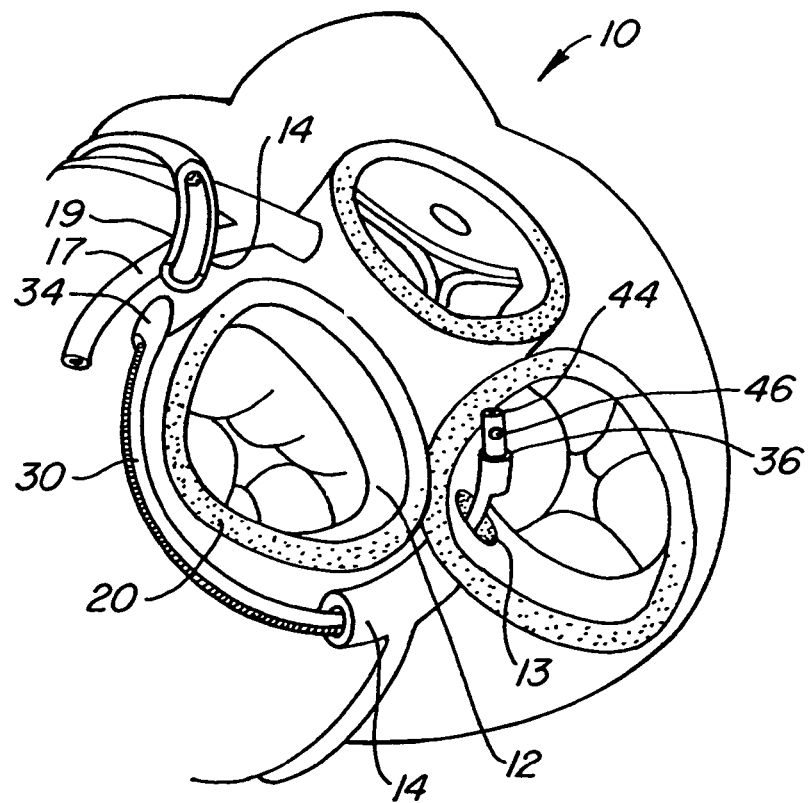
FIG. 8 is another superior view of a human heart illustrating an implanted mitral valve therapy device embodying the present invention.

Once a device is deployed that satisfies the requirements of the procedure, the guide wire 52, and the wire 70 if still within the heart, may be removed. This leaves the device 30 in its proper position as illustrated in FIG. 8. Here it may be seen that the device 30 partially encircles the mitral valve 12 within the coronary sinus 14 and adjacent to the mitral valve annulus. The distal end 34 of the device 30 is proximal to the crossover point 19. The proximal end 36 of the device protrudes slightly into the right atrium (not shown) through the ostium of coronary sinus 13. The sleeve 44 and pin 46 remain should subsequent removal of the device be deemed necessary.

Figure 9:
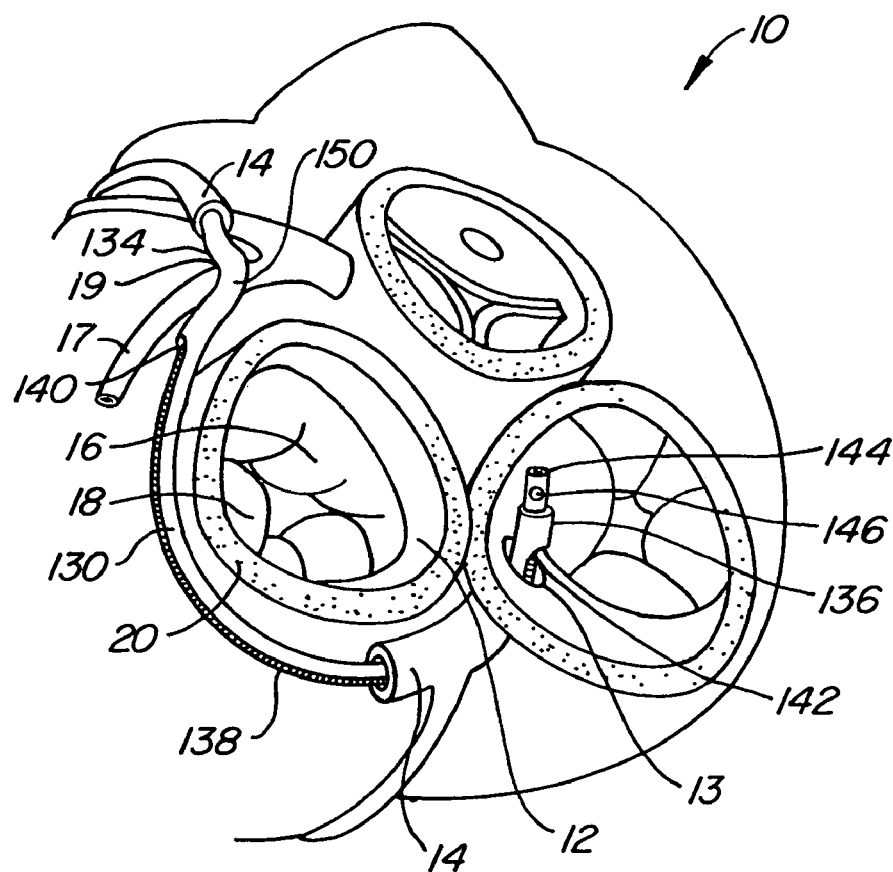
FIG. 9 is another superior view of a human heart illustrating another mitral valve therapy device embodying the present invention implanted in the heart.

FIG. 9 shows another mitral valve therapy device 130 embodying the present invention. As may be noted in FIG. 9, the device is elongated and has an arched configuration to at least partially encircle the mitral valve 12 adjacent to the mitral valve annulus 20 when implanted in the coronary sinus 14. The device 130 has an unstressed preformed arched radius smaller than the radius of the dilated mitral valve annulus 20 to impart an inward, generally radial force when implanted in the coronary sinus of the heart as shown. This force again returns the mitral valve annulus 20 to its original or substantially original geometry to permit the cusps 16 and 18 to more fully come together for sealing the left atrium during left ventricular contraction.

The device 130 has a cross sectional dimension to be received by the coronary sinus. It is also preferably formed of a resilient material to permit the device to be straightened and/or bent for being advanced into the coronary sinus. After being positioned within the coronary sinus, the device is permitted to assume its preformed arched configuration to act upon the mitral valve annulus as previously described.

To that end, the device may be formed of, for example, Nitinol, a nickel titanium alloy.

The device 130 has a distal end 134 and a proximal end 136. Between the distal end 134 and proximal end 136 the device further includes a channel 138 which is aligned with a bore 140 extending through the distal end 134 and a bore 142 extending through the proximal end 136. The proximal end 136 further includes an integral sleeve 144 which carries a protruding locking pin 146. Again, the bores 140 and 142 permit the device to be slidingly received by a guide wire during deployment of the device 130. The guide wire, during deployment, is confined within the channel 138.

The device 130 still further includes a bend 50 at its distal end 134. As will be noted, the distal end 134 extends beyond the crossover point 19 of the circumflex artery 17 and the coronary sinus 14. However, because of the bend 150, the device is precluded from exerting constricting pressure on the circumflex artery 17 even though it extends over the crossover point 19. The device 130 may be implanted using the assembly as previously described.

Figure 10:
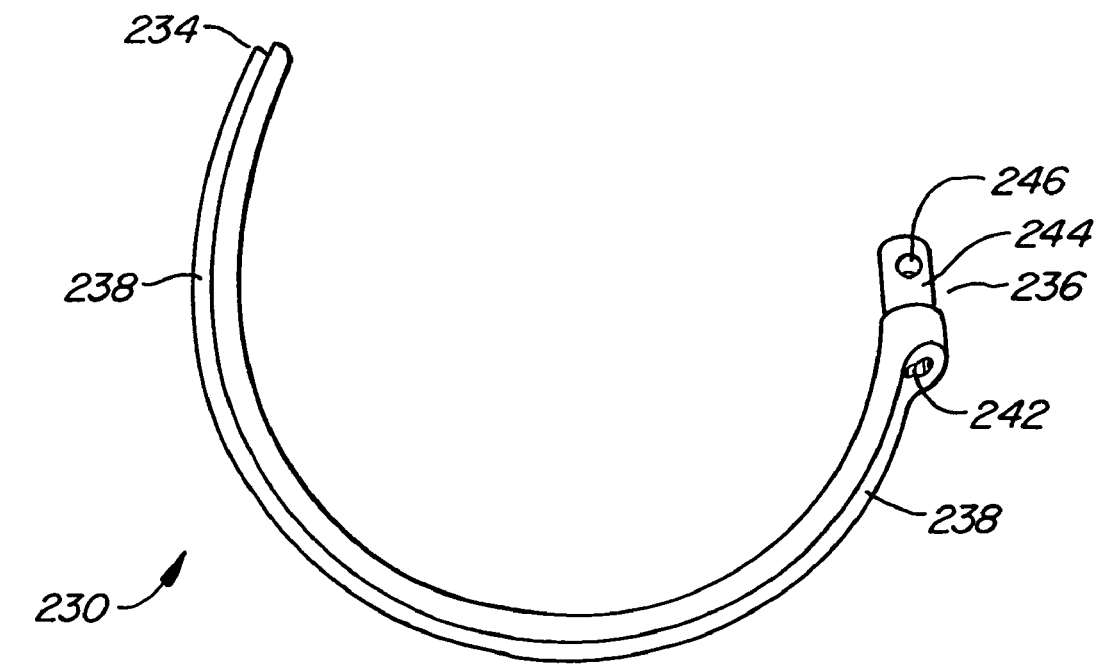
FIG. 10 is a perspective view of another mitral valve annulus device embodying the present invention.

FIG. 10 shows still another mitral valve therapy device 230 embodying the present invention. Like the device 30 of FIG. 2, the device 230 is elongated and has an arched configuration to at least partially encircle the mitral valve 12 adjacent to the mitral valve annulus 20 when implanted in the coronary sinus 14. The device 230 has an unstressed preformed arched radius smaller than the radius of the dilated mitral valve annulus 20 to impart an inward, generally radial force on the mitral valve annulus 20 when implanted in the coronary sinus of the heart to return the mitral valve annulus 20 to its original or substantially original geometry permitting the cusps of the mitral valve to more fully come together for sealing the left atrium during left ventricular contraction.

The device 230 has a cross section dimension to be received by the coronary sinus. It is preferably formed of any of the resilient materials previously described.

The device 230 has a distal end 234 and a proximal end 236. Between the distal end 234 and proximal end 236 the device further includes a channel 238 which is aligned with a bore 242 extending through the proximal end 236. The proximal end 236 further includes an integral sleeve 244 which carries a protruding locking pin 246. The bore 242 permits the device to be slidingly received by the guide wire during deployment of the device 230. The guide wire, during deployment, is confined within the channel 238. The assembly 50 of FIGS. 3 and 4 including the guide wire 52, guide tube 54, and elongated introducer 56 may be utilized as described for deploying the device 230. Here, however, only one end of the device need be slidingly received by the guide wire 52 since the device is well confined within the guide tube 54 and the guide wire 52 is confined within the channel 238.

As can thus be seen from the foregoing, the present invention provides a new and improved device, assembly and method for treating mitral regurgitation. The device may be employed with only percutaneous techniques. Further, the mitral valve therapy device may be implanted in a manner which avoids the crossover point of the circumflex artery and coronary sinus. Lastly, the effectiveness of the therapy may be immediately deduced during the implant procedure and permits substitution of devices for optimized results.

While particular embodiments of the present invention have been shown and described, modifications may be made, and it is therefore intended in the appended claims to cover all such changes and modifications which fall within the true spirit and scope of the invention.

What is claimed is:

1. A method of determining a crossover point of a circumflex artery and coronary sinus of a heart, the method including the steps of:
   inserting a first elongated flexible rod into the coronary sinus, the first rod being visible under X ray fluoroscopy;
   inserting a second elongated flexible rod into the circumflex artery, the second rod being visible under X ray fluoroscopy; and
   subjecting the heart to X ray fluoroscopic examination to determine the crossover point of the first and second rods.

2. A method of deploying a mitral valve annulus therapy device within a coronary sinus of a heart, the method including the steps of:
   inserting a first wire into a circumflex artery of the heart, the first wire being visible under X ray fluoroscopy;
   inserting a second wire into the coronary sinus of the heart, the second wire being visible under X ray fluoroscopy;
   subjecting the heart to X ray fluoroscopic examination to visualize a crossover point of the first and second wires; and
   deploying an elongated mitral valve annulus therapy device within the coronary sinus in a position such that a distal end of the device is proximal to the crossover point of the first and second wires.

3. The method of claim 2 wherein the deploying step includes guiding the device into the coronary sinus on the second wire.

4. The method of claim 3 wherein the deploying step further includes the steps of slidingly mounting an elongated flexible introducer onto the second wire proximal to the device, engaging the distal end of the introducer with the proximal end of the device, and pushing the device distally into the coronary sinus with the introducer.

5. The method of claim 4 including the further step of withdrawing the introducer after deploying the device.

6. The method of claim 5 wherein the engaging step includes releasably locking the proximal end of the device to the distal end of the introducer.

7. The method of claim 6 including the further step of releasing the proximal end of the device from the distal end of the introducer prior to withdrawing the introducer.

8. The method of claim 4 including the further steps of: providing an elongated flexible guide tube having an inner lumen, the inner lumen having a cross sectional dimension greater than the cross sectional dimension of the second wire, and the guide tube being transparent to X ray fluoroscopy; feeding the guide tube into the coronary sinus of the heart over the second wire with the second wire within the inner lumen of the guide tube; and wherein the pushing step includes pushing the device along the second wire and within the guide tube.

9. The method of claim 8 wherein the engaging step includes releasably locking the proximal end of the device to the distal end of the introducer.

10. The method of claim 9 including the further steps of releasing the proximal end of the device from the distal end of the introducer and withdrawing the introducer and the guide tube after deploying the device.

11. A method of deploying a mitral valve annulus therapy device within a coronary sinus of a heart, the method including the steps of:
    determining a crossover point between two coronary arteries; and
    deploying the mitral valve annulus therapy device within the coronary sinus in a position such that a distal end of the device is proximal to the crossover point.

* * * * *